United States Patent [19]

Kang et al.

[11] Patent Number: 5,176,848
[45] Date of Patent: Jan. 5, 1993

[54] CORROSION CONTROL COMPOSITION

[75] Inventors: Hyung H. Kang, Northbrook, Ill.; David B. Markobrad; Eugene A. Weipert, both of Kenosha, Wis.

[73] Assignee: PPG Industries, Inc., Pittsburgh, Pa.

[21] Appl. No.: 807,804

[22] Filed: Dec. 13, 1991

Related U.S. Application Data

[62] Division of Ser. No. 590,092, Sep. 28, 1990, abandoned.

[51] Int. Cl.$^5$ ............................................. C23F 11/14
[52] U.S. Cl. ..................... 252/389.62; 252/392; 422/16; 422/17
[58] Field of Search ........... 252/396, 390, 392, 389.62; 422/16, 17

[56] References Cited

U.S. PATENT DOCUMENTS

| | | | |
|---|---|---|---|
| 2,133,734 | 10/1938 | Moser | 252/396 X |
| 2,411,215 | 11/1946 | Kise et al. | 260/342.4 |
| 3,412,111 | 11/1968 | Irwin et al. | 260/346.5 |
| 3,762,873 | 10/1973 | Oude Alink | 252/392 X |
| 4,116,643 | 9/1978 | Ryer et al. | 252/392 X |
| 4,609,531 | 9/1986 | Ritschel et al. | 252/392 |
| 4,876,152 | 10/1989 | Kang | 428/447 |
| 4,956,498 | 9/1990 | Fakoukakis et al. | 549/255 |
| 5,021,169 | 6/1991 | Shin et al. | 549/255 |

FOREIGN PATENT DOCUMENTS

| | | |
|---|---|---|
| 0319809 | 11/1988 | European Pat. Off. |
| 52-25102 | 2/1977 | Japan |
| 55-6759 | 2/1980 | Japan |
| 64-79163 | 3/1989 | Japan |

*Primary Examiner*—Richard D. Lovering
*Assistant Examiner*—Valerie Fee
*Attorney, Agent, or Firm*—Edward J. Whitfield; George D. Morris

[57] ABSTRACT

Disclosed are compositions comprising the reaction product of maleic anhydride and at least one alkenylsuccinic anhydride. These compositions when hydrolyzed and neutralized are useful in not only imparting corrosion resistance to ferrous metal surfaces in contact with aqueous systems but also retard or prevent precipitation of alkaline earth salts of organic acids from the aqueous system.

20 Claims, No Drawings

CORROSION CONTROL COMPOSITION

This application is a continuation of application Ser. No. 07/590,092, filed Sep. 28, 1990 now abandoned.

FIELD OF THE INVENTION

This invention relates to novel compositions comprising alkenylsuccinic anhydride derivatives, which compositions when added to water or aqueous systems, such as, water-containing liquids that are in contact with metal surfaces, i.e., ferrous metal surfaces, not only protect the metal surfaces from corrosion but also serve as a chelating or sequestering agent to retard precipitation of alkaline earth salts of organic acids contained in the water or water-containing liquid.

Alkenylsuccinic anhydrides are known compounds and have a variety of uses, such as, e.g., as corrosion inhibitors in water based lubricating fluids used in the metal working industry; and as corrosion inhibitors in antifreeze and cooling water systems. They are also used in water repellent compositions such as described in U.S. Pat. No. 4,876,152 which discloses the reaction product of linear polysiloxanes with alkenylsuccinic anhydrides.

This invention provides novel compositions having both corrosion inhibiting as well as sequestering properties, which compositions are hydrolyzed, neutralized, reaction products of maleic anhydride and at least one alkenylsuccinic anhydride.

DESCRIPTION OF THE INVENTION

In accordance with one embodiment of this invention, maleic anhydride is reacted with alkenylsuccinic anhydride containing a total of from 10 to 30 carbon atoms to produce a reaction product which is then hydrolyzed. In a further embodiment, the hydrolyzed reaction product is neutralized to form a composition of the invention having corrosion inhibiting and sequestering properties. While alkenylsuccinic anhydrides containing more than 30 carbon atoms may be used, readily available alkenylsuccinic anhydrides are those containing from 10 to 30 carbon atoms and preferably from 12 to 20 carbon atoms. Octenylsuccinic anhydride and dodecenylsuccinic anhydride are exemplary of materials suitable for use in preparing the compositions of the invention. Alkenylsuccinic anhydrides are typically prepared by reacting maleic anhydride with a molar excess of 1-monoolefin, as described, e.g., in U.S. Pat. No. 3,412,111.

In accordance with the invention, the mole ratio of maleic anhydride to alkenylsuccinic anhydride may vary from about 0.05:1 up to about 1:1 and preferably from about 0.15:1 up to about 0.40:1. Reaction of alkenylsuccinic anhydride with maleic anhydride may be effected in any suitable reaction vessel at a temperature of from about 200° C. to about 260° C., preferably from about 210° C. to about 225° C. If desired, the reaction may be conducted at elevated pressure of, e.g., up to about 100 psig. The progress of the reaction is monitored by periodic determination of the free maleic anhydride content and is preferably terminated when the free maleic anhydride content becomes less than about 1.5 weight percent and the total solids content of the reaction product is preferably about 97 weight percent. Typical reaction time ranges from about 5 to about 10 or so hours. The reaction product is then cooled to between about 150° to 160° C. and vacuum stripped to remove unreacted maleic anhydride. The maleic anhydride-alkenylsuccinic anhydride reaction product is readily hydrolyzed by the addition of water and heating at a temperature of from about 50° C. up to about 100° C. although the temperature is not particularly critical. Hydrolysis may, if desired be effected in the presence of a catalytic amount of a water soluble alkaline material, e.g., alkali metal hydroxide, such as sodium or potassium hydroxide. Typically, from about 0.05 to about 1.0 weight percent of alkali metal hydroxide is used. Completion of hydrolysis is evidenced by the reaction mixture turning from cloudy to clear. The quantity of water used to hydrolyze the reaction product is likewise not all that critical and may range from about 10 to about 50 percent by weight based on the combined weight of water and anhydride reaction product. Preferably water is present in amounts of from about 25 to about 35 weight percent based on the combined weight of water and anhydride reaction product.

To prepare a composition of the invention having corrosion inhibiting and sequestering properties, the hydrolyzed product is neutralized by the addition of a suitable water soluble alkaline reagent selected from the group consisting of monoethanolamine, diethanolamine, triethanolamine, morpholine, potassium hydroxide, sodium hydroxide, and mixtures thereof. Sufficient base is used to adjust the pH of the hydrolyzed reaction mixture in the range of from about 6.0 to 9.0 and preferably in the range of from about 6.8 to 8.0. To facilitate handling and metering, the neutralized product may be further diluted with an inert diluent that is non-reactive with the neutralized hydrolysis product. Water is a preferred diluent. The amount of diluent is not particularly critical and may vary over a wide range, e.g., from about 5 to about 95 weight percent, preferably from about 10 to about 30 weight percent, based on the combined weight of diluent and neutralized product.

Alternatively, the compositions of the invention may be prepared by reacting a 1-monoolefin with a molar excess of maleic anhydride. The reaction between the monoolefin and maleic anhydride is conducted under substantially the same conditions as the above described reaction between maleic anhydride and alkenylsuccinic anhydride. The 1-monoolefin may be linear or branched and contains from 6 to 26, preferably from 8 to 16 carbon atoms. Exemplary monoolefins include 1-octene, 1-dodecene, 1-tetradecene, 1-hexadecene, or the like. About 1.1 and up to about 1.5 moles of maleic anhydride are used per mole of 1-monoolefin. The reaction product of the monoolefin and maleic anhydride is then hydrolyzed, neutralized and/or further diluted as described hereinabove to form a composition of the invention.

For commercial applications, the compositions of the invention typically contain from about 10 to about 30 weight percent of hydrolyzed maleic anhydride-alkenylsuccinic anhydride reaction product, the balance comprising sufficient of the neutralizing agent to adjust the pH in the requisite range, and diluent. Preferred compositions of the invention contains about 20 to about 30 weight percent of hydrolyzed maleic anhydride-alkenylsuccinic anhydride reaction product, the balance comprising neutralizing agent and diluent. A most preferred composition of the invention comprises about 20 weight percent of the hydrolyzed reaction product of about 0.21 mole of maleic anhydride per mole of octenylsuccinic anhydride, about 60 weight percent of triethanolamine neutralizing agent, and about 20 weight percent of diluent water. This composition is a brown liquid having a Brookfield viscosity of about 500 cps at 23° C., a density of about 1.14 at 23° C. and a pH of about 7.6.

When used to prevent corrosion of ferrous metal surfaces in contact with aqueous systems, the quantity of invention composition required may vary over a wide range, but a corrosion inhibiting amount can readily be determined by those skilled in the art. Typically the addition of from about 0.5 to about 1.5 weight percent of the invention composition should provide satisfactory corrosion control in most cases. As beforesaid, in addition to providing corrosion control, the invention compositions also function as sequestering or chelating agents by preventing or retarding precipitation of alkaline earth salts of organic acids in the water or aqueous system being treated. As a consequence, the invention compositions are particularly useful with so-called "hard" water, i.e., water containing dissolved alkaline earths, principally calcium and magnesium which form precipitates in the presence of organic acids. The amount of dissolved alkaline earths in the water or water hardness is conventionally expressed as parts per million (ppm) of calcium carbonate ($CaCO_3$). It has been observed that such precipitates will form in water containing as little as about 40 ppm $CaCO_3$ hardness. When so used, sufficient of the invention composition is present to retard or prevent such precipitation, the optimal quantity again being capable of ready determination by those skilled in the art.

The invention compositions may also be used with other commercially used water treatment chemicals. For example, $C_8$ to $C_{10}$ monocarboxylic acids such as caprylic acid; and $C_{10}$ to $C_{12}$ dicarboxylic acids such as dodecanedioic acid or octenylsuccinic acid are conventionally used as corrosion control additives in aqueous systems. These acids are used in the form of water soluble salts neutralized with, e.g. triethanolamine or other water soluble alkaline reagents such as those mentioned hereinabove. Although providing adequate corrosion control, in hard waters these carboxylic acids form water insoluble precipitates. It has been found that when the invention compositions are formulated with such hard water unstable corrosion control chemicals, not only is excellent corrosion control obtained but undesirable precipitation is prevented or substantially retarded. Such formulations can typically contain from about 5 to about 30 weight percent of invention composition and from about 5 to about 40 weight percent of said mono or dicarboxylic acids.

The invention is further illustrated, but is not intended to be limited, by the following Examples.

EXAMPLE 1

A mixture of 1319 grams (6.28 moles) of octenylsuccinic anhydride and 308 grams (3.14 moles) of maleic anhydride was heated at a temperature of 220° C. to 230° C. for about 6 hours, after which the reaction mixture was stripped, under a nitrogen sparge, for about 4 hours at about 150° C. to remove any unreacted starting maleic anhydride, affording about 1595 grams of precursor product. About 3.5 grams of potassium hydroxide dissolved in about 3.0 milliliters of water were added to the this product and the same was heated to about 120° C., after which about 114 grams of water was slowly added at 120° to 135° C. After standing overnight, an additional 453 grams of water were added and the mixture was heated for about 3 hours at about 80° C. The reaction mixture was cooled and an additional 2.5 grams of water was added to adjust the hydrolyzed anhydrides reaction mixture concentration to about 70 weight percent. The hydrolyzed reaction mixture was neutralized with triethanolamine to a pH of 7 to 8 and diluted with water to form a composition containing about 28.57 weight percent of hydrolyzed anhydrides reaction product, about 60 weight percent triethanolamine and about 11.43 weight percent of diluent water.

EXAMPLE 2

To a Parr reactor were charged about 660 grams (5.89 moles) of 1-octene and about 840 grams (8.57 moles) of maleic anhydride. The reaction mixture was heated to about 200° C. at a pressure of about 75 psi and heating was continued at about 225° C. and at a pressure of about 100 psi for about 24 hours. The reaction mixture was then stripped at a temperature of about 160° C., under a water aspirator vacuum, for about 2 hours to remove any unreacted starting materials. The vacuum stripped material was mixed with 4.0 grams of potassium hydroxide and 200 grams of water and heated at a temperature of about 100° C. until a clear solution was obtained. After cooling, the hydrolyzed reaction mixture sufficient water was added so as to adjust the hydrolyzed anhydride reaction product to about 70 weight percent. The hydrolyzed reaction product was then neutralized to a pH of from 7 to 8 with triethanolamine and diluted with water to form a composition containing about 28.57 weight percent of hydrolyzed 1-octene-maleic anhydride reaction product, about 60 weight percent of triethanolamine and about 11.43 weight percent of diluent water.

EXAMPLE 3 (Comparison)

Octenylsuccinic anhydride was hydrolyzed and neutralized to a pH of from 7 to 8 in accordance with the procedure described in Example 1 to form a product containing about 28.57 weight percent of hydrolyzed octenylsuccinic anhydride, about 60 weight percent of triethanolamine neutralizing agent and about 11.43 weight percent of diluent water.

EXAMPLE 4

A simulated hard water was prepared by mixing 75 parts of tap water having a hardness of about 100 ppm $CaCO_3$ with 25 parts of an aqueous solution containing about 0.66 gram per liter of calcium chloride dihydrate. To equal aliquots of the hard water were added:

A. 0.9 weight percent of the Example 1 composition;
B. 0.9 weight percent of the Example 2 composition;
C. 0.9 weight percent of the Example 3 composition;
D. 0.45 weight percent each of the Example 1 and Example 3 compositions; and
E. 0.45 weight percent each of the Example 2 and Example 3 compositions.

To each of test solutions A to E were added about 20 grams of cast iron chips having an average size of about 0.3 cm. The chips were swirled in the test solutions for about 30 seconds, drained and spread on clean mild steel plates. After about 24 hours, the number of rust spots on each plate were tabulated. Also, the appearance of any precipitate (ppt.) in each of the test solutions was visually evaluated. The results are as follows:

| Test Mixture | No. of Spots | Appearance |
|---|---|---|
| A. | 16 | Clear |
| B. | 20 | Slight ppt. |
| C. | 30+ | Heavy ppt. |
| D. | 14 | Clear |
| E. | 20 | Slight ppt. |

As the test results show, the invention compositions when used either alone (A. and B.) or in combination with known corrosion control agent (D. and E.) in the presence of hard water provide not only good corrosion control but also retard or prevent precipitation of calcium salts of organic acids as compared to use of said known corrosion control agent (C.).

EXAMPLE 5

To a 2-liter, round bottom flask provided with a stirrer, a thermometer and a condenser, were charged about 968 grams (4.61 moles) of octenylsuccinic anhydride and about 25.7 grams (0.26 mole) of maleic anhydride. After heating for about 6 hours at 220° to 230° C., the reaction mixture was cooled to about 150° C. and sparged with nitrogen for about 3 hours at about 150° C. to remove any unreacted maleic anhydride. About 265.3 grams of the reaction product was hydrolyzed by adding about 113.4 grams of water containing about 0.3 gram of potassium hydroxide. The resulting mixture was then heated at about 75° C. for about 2 days to obtain a clear solution. About 47.5 grams of the hydrolyzed reaction mixture was mixed with about 99.75 grams of triethanolamine and about 19 grams of water to form a product having a pH in the range of 7 to 8 and containing about 60 weight percent of triethanolamine, about 20 weight percent of hydrolyzed anhydrides reaction product and about 20 weight percent of diluent water.

EXAMPLE 6

A simulated hard water was prepared by mixing about 98 parts of tap water having a hardness of about 100 ppm $CaCO_3$ with about 15 parts of an aqueous solution containing about 2.94 grams per liter of calcium chloride dihydrate. The following test solutions were prepared:

A. About 2.0 grams of the composition of Example 5 in about 98 milliliters of tap water;
B. About 2.0 grams of a composition containing about 20 weight percent of hydrolyzed octenylsuccinic anhydride, about 60 weight percent of triethanolamine and about 20 weight percent of diluent water in about 98 milliliters of tap water;
C. About 2.0 grams of a composition containing about 20 weight percent of dodecanedioic acid, about 60 weight percent of triethanolamine and about 20 weight percent of diluent water in about 113 milliliters of simulated hard water;
D. About 4.0 grams of a composition containing about 20 weight percent of caprylic acid, about 60 weight percent of triethanolamine and about 20 weight percent of diluent water in about 113 milliliters of simulated hard water;
E. About 2.0 grams each of Composition A. and Composition C. in about 113 milliliters of simulated hard water; and
F. About 2.0 grams each of Composition A. and Composition D. in about 113 milliliters of simulated hard water.

The appearance of any precipitate (ppt.) in each test solution A. to F. was visually evaluated after 30 minutes and 24 hours with the following results:

| Solution | Appearance | |
|---|---|---|
| | 30 min. | 24 hrs. |
| A. | Clear | Clear |
| B. | Heavy ppt. | Heavy ppt. |
| C. | Heavy ppt. | Heavy ppt. |
| D. | Heavy ppt. | Heavy ppt. |
| E. | Clear | Clear |
| F. | Clear | Slight ppt. |

As the above results show, the invention composition when used alone (A.) or in admixture with known corrosion control agents (E., F.) either retard or prevents precipitation of calcium salts of organic acids as compared to known corrosion control agents (B., C., D.)

EXAMPLE 7

About 3354 grams (15.97 moles) of octenylsuccinic anhydride and about 782.6 grams (7.99 moles) of maleic anhydride were heated for about 8 hours at 220° to 225° C. followed by vacuum stripping for about 2 hours at about 200° C. to remove any unreacted starting materials. About 1514 grams of the stripped product were further vacuum stripped at about 160° to 180° C. using a 5-inch Vigreux column. The residue was neutralized with triethanolamine to a pH between 7 and 8 and diluted with water affording a product containing about 25 weight percent of stripped, hydrolyzed anhydrides, about 50 weight percent of triethanolamine and about 25 weight percent of diluent water. This product was further mixed with DBA 101 dodecanedioic acid (product of E. I. DuPont de Nemours and Co.) and caprylic acid, the resulting formulation assaying about 7.0 weight percent of hydrolyzed anhydrides, about 7.0 weight percent of DBA 101, about 16 weight percent of caprylic acid, about 50 weight percent of triethanolamine and about 20 weight percent of diluent water. Both good corrosion inhibition as well as good hard water stability were observed using this composition in laboratory tests as described hereinabove.

Although the invention is described in some detail by the foregoing Examples, the same are intended to be illustrative of the invention and not to constitute any limitation thereon; since many variations therein will be apparent to those skilled in the art without departing from the spirit and scope of the invention as defined by the appended claims.

We claim:

1. A method for inhibiting corrosion of ferrous metal in contact with water or a water containing liquid by adding to the water or water containing liquid a corrosion inhibiting amount of a composition comprising the hydrolyzed reaction product in which maleic anhydride has been reacted with octenylsuccinic anhydride in the ratio of from about 0.05 to about 1.0 mole of maleic anhydride per mole of octenylsuccinic anhydride wherein the pH of said hydrolyzed reaction product has been adjusted to be in the range of from about 6.0 to about 9.0 with water soluble alkaline reagent selected from the group consisting of monoethanolamine, diethanolamine, triethanolamine, morpholine, potassium hydroxide, sodium hydroxide, and mixtures thereof.

2. The method of claim 1 wherein the pH of said hydrolyzed reaction product has been adjusted to be in the range of from about 6.8 to about 8.0 with said water soluble alkaline reagent.

3. The method of claim 2 wherein said water soluble alkaline reagent is triethanolamine.

4. The method of claim 1 wherein said composition comprises the hydrolyzed reaction product in which maleic anhydride has been reacted with octenylsuccinic anhydride in the ratio of from about 0.15 to about 0.40 mole of maleic anhydride per mole of octenylsuccinic anhydride wherein the pH of said hydrolyzed reaction product has been adjusted to be in the range of from about 6.0 to about 9.0 with water soluble alkaline reagent selected from the group consisting of monoethanolamine, diethanolamine, triethanolamine, morpholine, potassium hydroxide, sodium hydroxide, and mixtures thereof.

5. The method of claim 4 wherein the pH of said hydrolyzed reaction product has been adjusted to be in the range of from about 6.8 to about 8.0 with water soluble alkaline reagent.

6. The method of claim 5 wherein said water soluble alkaline reagent is triethanolamine.

7. The method of claim 4 wherein said water soluble alkaline reagent is triethanolamine.

8. The method of claim 1 wherein said water soluble alkaline reagent is triethanolamine.

9. A method for inhibiting corrosion of ferrous metal in contact with water or a water containing liquid by adding to the water or water containing liquid a corrosion inhibiting amount of a composition comprising the hydrolyzed reaction product in which maleic anhydride has been reacted with octenylsuccinic anhydride in the ratio of about 1.0 mole of maleic anhydride per mole of octenylsuccinic anhydride wherein the pH of said hydrolyzed reaction product has been adjusted to be in the range of from about 6.0 to about 9.0 with water soluble alkaline reagent selected from the group consisting of monoethanolamine, diethanolamine, triethanolamine, morpholine, potassium hydroxide, sodium hydroxide, and mixtures thereof.

10. The method of claim 9 wherein the pH of said hydrolyzed reaction product has been adjusted to be in the range of from about 6.8 to about 8.0 with said water soluble alkaline reagent.

11. The method of claim 10, wherein said water soluble alkaline reagent is triethanolamine.

12. The method of claim 9 wherein said water soluble alkaline reagent is triethanolamine.

13. A method for inhibiting corrosion of ferrous metal in contact with water or a water containing liquid by adding to the water or water containing liquid a corrosion inhibiting amount of a composition comprising the hydrolyzed reaction product of 1-octene with a molar excess of maleic anhydride wherein the pH of said hydrolyzed reaction product has been adjusted to be in the range of from about 6.0 to about 9.0 with water soluble alkaline reagent selected from the group consisting of monoethanolamine, diethanolamine, triethanolamine, morpholine, potassium hydroxide, sodium hydroxide, and mixtures thereof.

14. The method of claim 13 wherein the pH of said hydrolyzed reaction product has been adjusted to be in the range of from about 6.8 to about 8.0 with said water soluble alkaline reagent.

15. The method of claim 14 wherein said water soluble alkaline reagent is triethanolamine.

16. The method of claim 13 wherein said composition comprises the hydrolyzed reaction product in which maleic anhydride has been reacted with 1-octene in the ratio of from about 1.1 to about 1.5 moles of maleic anhydride per mole of 1-octene wherein the pH of said hydrolyzed reaction product has been adjusted to be in the range of from about 6.0 to about 9.0 with water soluble alkaline reagent selected from the group consisting of monoethanolamine, diethanolamine, triethanolamine, morpholine, potassium hydroxide, sodium hydroxide, and mixtures thereof.

17. The method of claim 16 wherein the pH of said hydrolyzed reaction product has been adjusted to be in the range of from about 6.8 to about 8.0 with said water soluble alkaline reagent.

18. The method of claim 17 wherein said water soluble alkaline reagent is triethanolamine.

19. The method of claim 16 wherein said water soluble alkaline reagent is triethanolamine.

20. The method of claim 13 wherein said water soluble alkaline reagent is triethanolamine.

* * * * *